US009962065B2

(12) United States Patent
Koshika (10) Patent No.: US 9,962,065 B2
(45) Date of Patent: May 8, 2018

(54) OPTICAL SCANNING OBSERVATION SYSTEM WITH DRIVE VOLTAGE CORRECTION

(71) Applicant: OLYMPUS CORPORATION, Tokyo (JP)

(72) Inventor: Soichiro Koshika, Mitaka (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days. days.

(21) Appl. No.: 15/291,139

(22) Filed: Oct. 12, 2016

(65) Prior Publication Data

US 2017/0027423 A1 Feb. 2, 2017

Related U.S. Application Data

(63) Continuation of application No. PCT/JP2015/074729, filed on Aug. 31, 2015.

(30) Foreign Application Priority Data

Nov. 10, 2014 (JP) .................................. 2014-228050

(51) Int. Cl.
| | |
|---|---|
| *A61B 1/06* | (2006.01) |
| *A61B 1/04* | (2006.01) |
| *A61B 1/00* | (2006.01) |
| *G02B 23/24* | (2006.01) |
| *G02B 26/10* | (2006.01) |

(52) U.S. Cl.
CPC ............ *A61B 1/00172* (2013.01); *A61B 1/00* (2013.01); *A61B 1/00004* (2013.01); *A61B 1/04* (2013.01);
(Continued)

(58) Field of Classification Search
CPC ... A61B 1/00172; A61B 1/00; A61B 1/00004; A61B 1/04; A61B 1/07; A61B 1/0623;
(Continued)

(56) References Cited

U.S. PATENT DOCUMENTS

| | | | |
|---|---|---|---|
| 7,612,330 B2 | 11/2009 | Ogikubo | |
| 2009/0060381 A1* | 3/2009 | Dunki-Jacobs | ...... A61B 1/0008 382/275 |

(Continued)

FOREIGN PATENT DOCUMENTS

| | | |
|---|---|---|
| EP | 3 138 464 A1 | 3/2017 |
| JP | 2009-063637 A | 3/2009 |

(Continued)

OTHER PUBLICATIONS

International Search Report dated Nov. 17, 2015 issued in PCT/JP2015/074729.

(Continued)

*Primary Examiner* — Anhtuan T Nguyen
*Assistant Examiner* — William Chou
(74) *Attorney, Agent, or Firm* — Scully, Scott, Murphy & Presser, P.C.

(57) ABSTRACT

An optical scanning observation system includes: an endoscope having an optical scanning portion for scanning an object; a drive signal generation portion configured to generate a drive signal and supply the signal to the optical scanning portion; an electric-current measurement portion configured to measure an electric current value of the drive signal; a first storage portion in which a measured electric current value when the temperature of the optical scanning portion is a predetermined temperature is stored; a second storage portion in which a plurality of parameters that are set according to the size of the measured electric current value are stored; and a correction processing portion configured to correct a scanning range of the endoscope by reading in from the second storage portion a parameter that corresponds to the size of the measured electric current value read in from the first storage portion.

4 Claims, 5 Drawing Sheets

(52) U.S. Cl.
CPC ......... *G02B 23/24* (2013.01); *G02B 23/2469* (2013.01); *G02B 26/103* (2013.01)

(58) Field of Classification Search
CPC ...... A61B 8/14; G02B 23/24; G02B 23/2469; G02B 26/103
USPC ....... 600/109, 117, 118, 160, 178, 179, 180, 600/181, 182; 250/234, 235, 236
See application file for complete search history.

(56) References Cited

U.S. PATENT DOCUMENTS

| | | | |
|---|---|---|---|
| 2009/0062659 A1* | 3/2009 | Weir | ................. A61B 1/00096 600/476 |
| 2010/0150591 A1 | 6/2010 | Yamashita | |
| 2011/0218437 A1 | 9/2011 | Park et al. | |

FOREIGN PATENT DOCUMENTS

| | | |
|---|---|---|
| JP | 2013-503724 A | 2/2013 |
| JP | 2014-145942 A | 8/2014 |
| JP | 2017-000193 A | 1/2017 |
| WO | WO 2011/031753 A2 | 3/2011 |
| WO | WO 2014/119288 A1 | 8/2014 |

OTHER PUBLICATIONS

Extended Supplementary European Search Report dated Dec. 5, 2017 in European Patent Application No. 15 85 8917.6.

\* cited by examiner

| MEASURED ELECTRIC CURRENT VALUE | FIRST COEFFICIENT | SECOND COEFFICIENT |
|---|---|---|
| $IA \leqq I < IB$ | $\alpha$ | $\beta$ |
| $IB \leqq I < IC$ | $\gamma$ | $\delta$ |
| ⋮ | ⋮ | ⋮ |

| MEASURED ELECTRIC CURRENT VALUE | ELECTRIC CURRENT THRESHOLD VALUE |
|---|---|
| $IA \leqq I < IB$ | IT1 |
| $IB \leqq I < IC$ | IT2 |
| ⋮ | ⋮ |

TB2

OPTICAL SCANNING OBSERVATION SYSTEM WITH DRIVE VOLTAGE CORRECTION

CROSS REFERENCE TO RELATED APPLICATION

This application is a continuation application of PCT/JP2015/074729 filed on Aug. 31, 2015 and claims benefit of Japanese Application No. 2014-228050 filed in Japan on Nov. 10, 2014, the entire contents of which are incorporated herein by this reference.

BACKGROUND OF THE INVENTION

1. Field of the Invention

The present invention relates to an optical scanning observation system, and more particularly to an optical scanning observation system that scans an object and acquires an image.

2. Description of the Related Art

Various technologies have been proposed for endoscopes used in medical fields in order to narrow the diameter of an insertion portion thereof which is inserted into a body cavity of a subject, and thereby reduce the burden of the subject. As one example of such technology, a scanning endoscope is known which does not have a solid-state image pickup device in a portion corresponding to the aforementioned insertion portion. Further, for example, Japanese Patent Application Laid-Open Publication No. 2009-63637 discloses an optical scanning probe apparatus which includes an optical scanning probe that corresponds to the aforementioned scanning endoscope.

Specifically, in Japanese Patent Application Laid-Open Publication No. 2009-63637, a configuration is disclosed for correcting a driving voltage applied to an optical scanning element while referring to the contents of a correction table in an optical scanning probe apparatus in which the optical scanning element which is configured to change a size of an angle of inclination of a minute mirror on which illuminating light from a light source is incident in accordance with a size of the driving voltage is arranged in a distal end portion of an optical scanning probe.

SUMMARY OF THE INVENTION

An optical scanning observation system according to one aspect of the present invention includes: an endoscope including an optical scanning portion for scanning an object with an illuminating light that is emitted from a light source portion; a drive signal generation portion configured to generate a drive signal that is in accordance with a driving voltage applied to the optical scanning portion; an electric-current measurement portion configured to measure an electric current value of the drive signal that is supplied from the drive signal generation portion to the optical scanning portion; a first storage portion in which a measured electric current value that is an electric current value which is measured by the electric-current measurement portion when a temperature of the optical scanning portion is a predetermined temperature is stored in advance; a second storage portion in which a plurality of correction parameters that are set in advance according to a size of the measured electric current value are stored; and a correction processing portion configured to read in from the second storage portion a correction parameter which corresponds to a size of the measured electric current value that is read in from the first storage portion, and perform correction processing for correcting a scanning range of the endoscope based on the correction parameter that is read in.

DETAILED DESCRIPTION OF THE PREFERRED EMBODIMENT(S)

An embodiment of the present invention is described hereunder with reference to the drawings.

Figure 1:
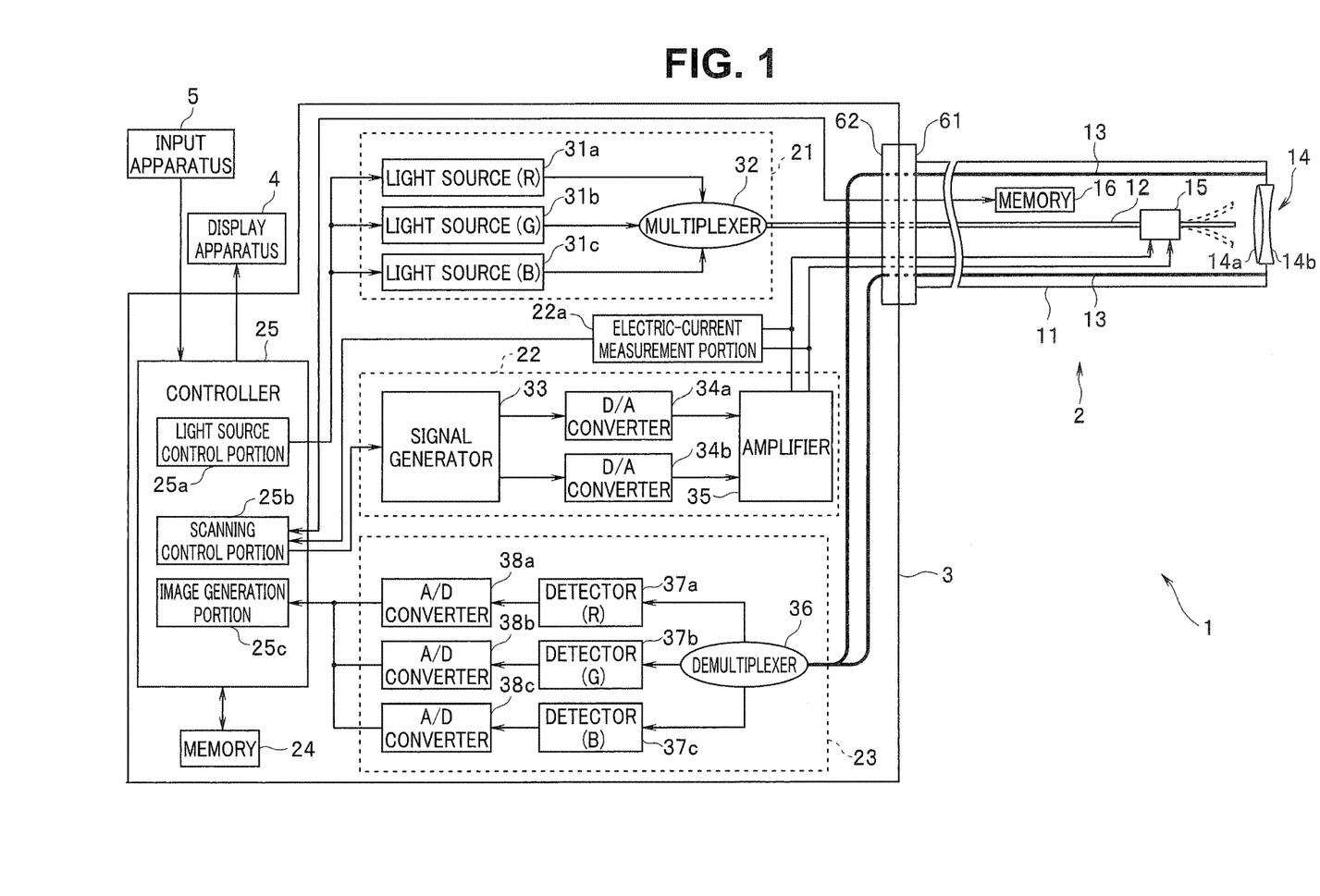
FIG. 1 is a view illustrating a configuration of the main part of an optical scanning observation system according to an embodiment.

FIG. 1 to FIG. 7 relate to an embodiment of the present invention. FIG. 1 is a view illustrating a configuration of a main part of an optical scanning observation system according to the embodiment.

As illustrated in FIG. 1, an optical scanning observation system 1 includes, for example, a scanning endoscope 2 to be inserted into a body cavity of a subject, a main body apparatus 3 configured to be connectable to the endoscope 2, a display apparatus 4 that is connected to the main body apparatus 3, and an input apparatus 5 configured to enable an input of information and provision of an instruction to the main body apparatus 3.

The endoscope 2 includes an insertion portion 11 formed to have an elongated shape that enables the insertion portion 11 to be inserted into a body cavity of a subject.

In a proximal end portion of the insertion portion 11, a connector portion 61 is provided for detachably connecting the endoscope 2 to a connector receiving portion 62 of the main body apparatus 3.

Although not illustrated in the drawing, an electrical connector apparatus for electrically connecting the endoscope 2 and the main body apparatus 3 is provided inside the connector portion 61 and the connector receiving portion 62. Further, although not illustrated in the drawing, an optical connector apparatus for optically connecting the endoscope 2 and the main body apparatus 3 is provided inside the connector portion 61 and the connector receiving portion 62.

An illumination fiber 12 that is an optical fiber that guides illuminating light supplied from a light source unit 21 of the main body apparatus 3 to an illumination optical system 14, and light receiving fibers 13 which include one or more optical fibers for receiving return light from an object and guiding the return light to a detection unit 23 of the main body apparatus 3 are respectively inserted through a section from the proximal end portion to a distal end portion inside the insertion portion 11.

An incident end portion including a light incident face of the illumination fiber 12 is disposed in a multiplexer 32 provided inside the main body apparatus 3. Further, an emitting end portion including a light emission face of the illumination fiber 12 is disposed in the vicinity of a light incident face of a lens 14a provided in the distal end portion of the insertion portion 11.

An incident end portion including a light incident face of each light receiving fiber 13 is fixedly disposed at the periphery of a light emission face of a lens 14b in a distal end face of the distal end portion of the insertion portion 11. Further, an emitting end portion including a light emission face of each light receiving fiber 13 is disposed in a demultiplexer 36 provided inside the main body apparatus 3.

The illumination optical system 14 is configured by including the lens 14a on which illuminating light that passed through the light emission face of the illumination fiber 12 is incident, and the lens 14b that emits the illuminating light that passed through the lens 14a to an object.

In a section that is partway along the illumination fiber 12 on the distal end portion side of the insertion portion 11, an actuator portion 15 that is driven based on a drive signal supplied from a driver unit 22 of the main body apparatus 3 is provided.

Figure 2:
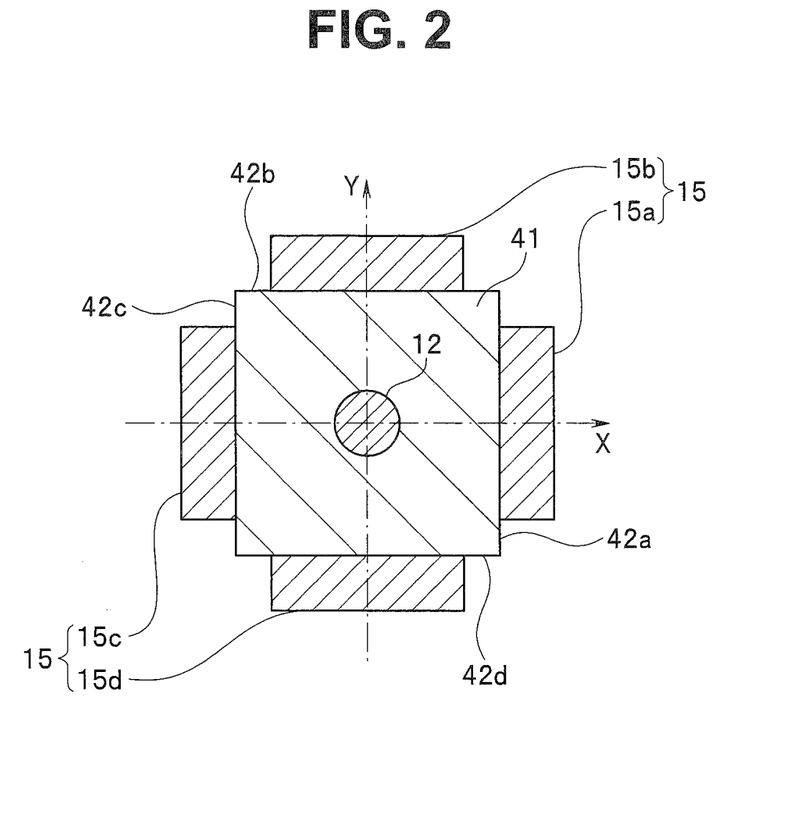
FIG. 2 is a cross-sectional diagram for describing a configuration of an actuator portion.

The illumination fiber 12 and the actuator portion 15 are respectively disposed so as to have, for example, a positional relationship illustrated in FIG. 2 in a cross-section perpendicular to a longitudinal axis direction of the insertion portion 11. FIG. 2 is a cross-sectional diagram for describing the configuration of the actuator portion.

As illustrated in FIG. 2, a ferrule 41 as a bonding member is disposed between the illumination fiber 12 and the actuator portion 15. More specifically, the ferrule 41 is formed of, for example, zirconia (ceramic) or nickel.

As illustrated in FIG. 2, the ferrule 41 is formed as a quadrangular prism, and includes side faces 42a and 42c that are perpendicular to an X-axis direction as a first axial direction that is orthogonal to the longitudinal axis direction of the insertion portion 11, and side faces 42b and 42d that are perpendicular to a Y-axis direction as a second axial direction that is orthogonal to the longitudinal axis direction of the insertion portion 11. The illumination fiber 12 is fixedly disposed at the center of the ferrule 41. Note that the ferrule 41 may be formed in a shape other than a quadrangular prism, as long as the ferrule 41 has a prism shape.

The actuator portion 15 that has a function as an optical scanning portion includes, for example, as illustrated in FIG. 2, a piezoelectric element 15a disposed along the side face 42a, a piezoelectric element 15b disposed along the side face 42b, a piezoelectric element 15c disposed along the side face 42c and a piezoelectric element 15d disposed along the side face 42d.

Each of the piezoelectric elements 15a to 15d has a polarization direction that is individually set in advance, and is configured to expand and contract in accordance with a driving voltage applied by a drive signal that is supplied from the main body apparatus 3.

A non-volatile memory 16 for storing measured electric current values (described later) that are unique to each endoscope 2 is provided inside the insertion portion 11. The measured electric current values stored in the memory 16 are read out by a controller 25 of the main body apparatus 3 when the connector portion 61 of the endoscope 2 and the connector receiving portion 62 of the main body apparatus 3 are connected and the power of the main body apparatus 3 is turned on. Note that, for example, the measured electric current values are stored in the memory 16 at an arbitrary timing before a timing at which a user first uses the endoscope 2, such as during manufacture of the endoscope 2 or the like.

The main body apparatus 3 is configured by including a light source unit 21, a driver unit 22, an electric-current measurement portion 22a, the detection unit 23, a memory 24 and the controller 25.

The light source unit 21 is configured by including a light source 31a, a light source 31b, a light source 31c and the multiplexer 32.

The light source 31a includes, for example, a laser light source, and is configured to emit light of a red wavelength band (hereinafter also referred to as "R light") to the multiplexer 32 when controlled to emit light by the controller 25.

The light source 31b includes, for example, a laser light source, and is configured to emit light of a green wavelength band (hereinafter also referred to as "G light") to the multiplexer 32 when controlled to emit light by the controller 25.

The light source 31c includes, for example, a laser light source, and is configured to emit light of a blue wavelength band (hereinafter also referred to as "B light") to the multiplexer 32 when controlled to emit light by the controller 25.

The multiplexer 32 is configured to multiplex the R light emitted from the light source 31a, the G light emitted from the light source 31b, and the B light emitted from the light source 31c, and supply the resultant multiplexed light to the light incident face of the illumination fiber 12.

The driver unit 22 is configured to generate a drive signal that is in accordance with a driving voltage that is applied to the actuator portion 15. The driver unit 22 is configured by including a signal generator 33, D/A converters 34a and 34b and an amplifier 35.

Figure 3:
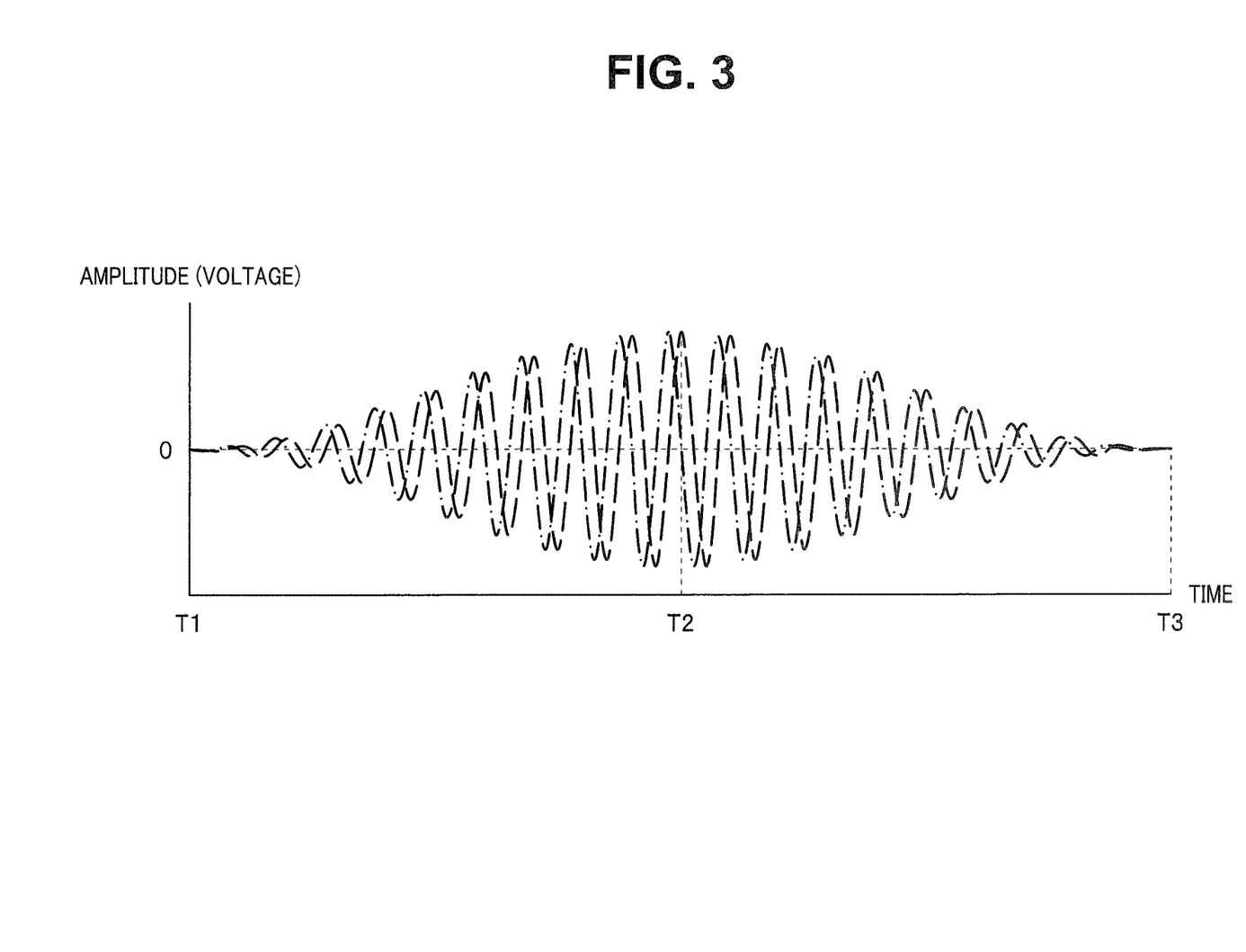
FIG. 3 is a view illustrating one example of a signal waveform of a drive signal that is supplied to the actuator portion.

The signal generator 33 is configured to generate a voltage signal having, for example, as shown by a dashed line in FIG. 3, a signal waveform obtained by performing predetermined modulation on a sine wave, as a first drive signal for swinging the emitting end portion of the illumination fiber 12 in the X-axis direction based on control of the controller 25, and to output the first drive signal to the D/A converter 34a. The signal generator 33 is also configured to generate a voltage signal having, for example, as shown by an alternate long and short dash line in FIG. 3, a signal waveform in which the phase of the first drive signal is shifted by 90° as a second drive signal for swinging the emitting end portion of the illumination fiber 12 in the Y-axis direction based on control of the controller 25, and to output the second drive signal to the D/A converter 34b. FIG. 3 is a view illustrating an example of signal waveforms of drive signals that are supplied to the actuator portion.

The D/A converter 34a is configured to convert the digital first drive signal that is outputted from the signal generator 33 to an analog first drive signal and to output the analog first drive signal to the amplifier 35.

The D/A converter 34b is configured to convert the digital second drive signal that is outputted from the signal generator 33 to an analog second drive signal and to output the analog second drive signal to the amplifier 35.

The amplifier 35 is configured to amplify the first and second drive signals outputted from the D/A converters 34a and 34b and output the resultant amplified drive signals to the actuator portion 15.

Figure 4:
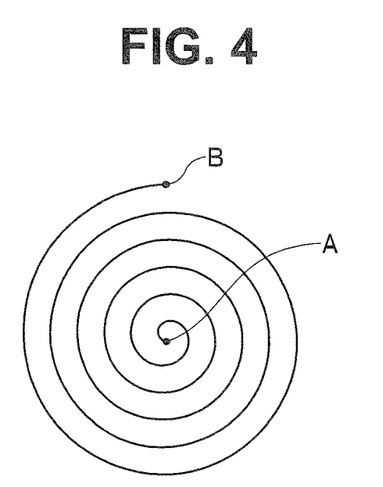
FIG. 4 is a view illustrating one example of a spiral scanning path from a center point A to an outermost point B.
Figure 5:
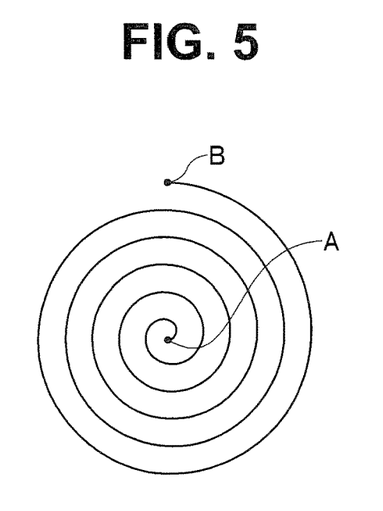
FIG. 5 is a view illustrating one example of a spiral scanning path from an outermost point B to a center point A.

In this case, for example, by application of a driving voltage in accordance with the first drive signal having a signal waveform as shown by the dashed line in FIG. 3 to the piezoelectric elements 15a and 15c of the actuator portion 15 as well as application of a driving voltage in accordance with the second drive signal having a signal waveform as shown by the alternate long and short dash line in FIG. 3 to the piezoelectric elements 15b and 15d of the actuator portion 15, the emitting end portion of the illumination fiber 12 is swung in a spiral shape, and the surface of the object is scanned along spiral scanning paths as shown in FIG. 4 and FIG. 5 in accordance with such swinging. FIG. 4 is a view illustrating an example of a spiral scanning path from a center point A to an outermost point B. FIG. 5 is a view illustrating an example of a spiral scanning path from the outermost point B to the center point A.

Specifically, first, at a time T1, an illuminating light is irradiated at a position corresponding to the center point A of the irradiation positions of illuminating light on the surface of the object. Thereafter, as the amplitudes (voltages) of the first and second drive signals increase from the time T1 to a time T2, the irradiation position of the illuminating light on the surface of the object changes so as to draw a first spiral scanning path to the outside that takes the center point A as the origin, and further, upon reaching the time T2, the illuminating light is irradiated onto the outermost point B of the irradiation positions of the illuminating light on the surface of the object. Subsequently, as the amplitudes (voltages) of the first and second drive signals decrease from the time T2 to a time T3, the irradiation position of the illuminating light on the surface of the object changes so as to draw a second spiral scanning path to the inside that takes the outermost point B as the origin, and further, upon reaching the time T3, the illuminating light is irradiated onto the center point A on the surface of the object.

That is, the actuator portion 15 has a configuration such that, by swinging the emitting end portion of the illumination fiber 12 based on the first and second drive signals supplied from the driver unit 22, the irradiation position of illuminating light emitted to an object via the emitting end portion is changed along the spiral scanning paths shown in FIG. 4 and FIG. 5. Furthermore, the amplitudes of the first and second drive signals supplied from the driver unit 22 to the actuator portion 15 become a maximum at the time T2 or in the vicinity of the time T2. Further, in a case where the spiral scanning paths shown in FIG. 4 and FIG. 5 are taken as an example, the scanning range of the endoscope 2 is shown as a region that belongs on the inner side relative to the path of an outermost periphery that includes the outermost point B of the spiral scanning path, and changes in accordance with the size of the maximum amplitude of the drive signals supplied to the actuator portion 15.

The electric-current measurement portion 22a is configured to measure an electric current value of the first drive signal supplied to the piezoelectric elements 15a and 15c of the actuator portion 15 from the driver unit 22, and to output the electric current value that is measured to the controller 25. Further, the electric-current measurement portion 22a is configured to measure an electric current value of the second drive signal supplied to the piezoelectric elements 15b and 15d of the actuator portion 15 from the driver unit 22, and to output the electric current value that is measured to the controller 25.

The detection unit 23 is configured by including the demultiplexer 36, detectors 37a, 37b and 37c, and A/D converters 38a, 38b and 38c.

The demultiplexer 36 includes a dichroic mirror or the like, and is configured to split return light that was emitted from the light emission face of each light receiving fiber 13 into light of the color components of R (red), G (green) and B (blue), and to emit the light of the color components of R (red), G (green) and B (blue) to the detectors 37a, 37b and 37c, respectively.

The detector 37a includes, for example, an avalanche photodiode, and is configured to detect an intensity of the R light outputted from the demultiplexer 36, generate an analog R signal according to the detected intensity of the R light, and output the analog R signal to the A/D converter 38.

The detector 37b includes, for example, an avalanche photodiode, and is configured to detect an intensity of the G light outputted from the demultiplexer 36, generate an analog G signal according to the detected intensity of the G light, and output the analog G signal to the A/D converter 38b.

The detector 37c includes, for example, an avalanche photodiode, and is configured to detect an intensity of the B light outputted from the demultiplexer 36, generate an analog B signal according to the detected intensity of the B light, and output the analog B signal to the A/D converter 38c.

The A/D converter 38a is configured to convert the analog R signal outputted from the detector 37a into a digital R signal and output the digital R signal to the controller 25.

The A/D converter 38b is configured to convert the analog G signal outputted from the detector 37b into a digital G signal and output the digital G signal to the controller 25.

The A/D converter 38c is configured to convert the analog B signal outputted from the detector 37c into a digital B signal and output the digital B signal to the controller 25.

Information including parameters such as amplitudes, frequencies and phase differences for identifying, for example, the signal waveforms in FIG. 3 is stored in the memory 24 as control information to be used when controlling the main body apparatus 3. A correction table that includes a plurality of amplitude correction parameters (described later) to be used when correcting amplitudes (respective amplitude including a maximum amplitude) of drive signals supplied to the actuator portion 15 from the driver unit 22 is also stored in the memory 24.

The controller 25 is constituted by, for example, an integrated circuit such as an FPGA (field programmable gate array). Further, the controller 25 is configured so as to be able to detect whether or not the insertion portion 11 is electrically connected to the main body apparatus 3 by detecting the connection state of the connector portion 61 at the connector receiving portion 62 through an unshown signal wire or the like. Further, the controller 25 includes a light source control portion 25a, a scanning control portion 25b and an image generation portion 25c.

The light source control portion 25a is configured to perform control with respect to the light source unit 21 so as to, for example, cause the light sources 31a to 31c to simultaneously emit light based on control information that is read in from the memory 24.

The scanning control portion 25b is configured to perform control with respect to the driver unit 22 so as to, for example, generate drive signals having the signal waveforms shown in FIG. 3 based on control information that is read in from the memory 24.

The scanning control portion 25b, for example, is configured to read in measured electric current values that are stored in the memory 16 when the connector portion 61 of the endoscope 2 and the connector receiving portion 62 of the main body apparatus 3 are connected and the power of the main body apparatus 3 is turned on. Further, the scanning control portion 25b is configured to read in an amplitude correction parameter that corresponds to the measured electric current values that are read in from the memory 16, from among the respective amplitude correction parameters included in the correction table stored in the memory 24. In addition, the scanning control portion 25b is configured to perform control with respect to the driver unit 22 so as to, based on an electric current value outputted from the electric-current measurement portion 22a and an amplitude correction parameter read in from the memory 24, generate drive signals which have corrected amplitudes which are obtained after amplitudes (respective amplitudes including a maximum amplitude) of drive signals supplied to the actuator portion 15 from the driver unit 22 are corrected in accordance with the relevant electric current value and the relevant amplitude correction parameter.

The image generation portion 25c is configured to, for example, detect a nearest scanning path based on a signal waveform of a drive signal that is generated in accordance with control of the scanning control portion 25b, specify a pixel position in raster-scan format that corresponds to an irradiation position of illuminating light on the detected scanning path, generate an observation image for one frame by mapping a luminance value indicated by a digital signal outputted from the detection unit 23 at the specified pixel position, and sequentially output the generated observation image for one frame to the display apparatus 4. The image generation portion 25c is also configured to enable the performance of processing for displaying a predetermined character string or the like as an image on the display apparatus 4.

The display apparatus 4 includes, for example, a monitor, and is configured to enable the display of an observation image that is outputted from the main body apparatus 3.

The input apparatus 5 includes, for example, a keyboard or a touch panel. Note that the input apparatus 5 may be configured as an apparatus that is separate from the main body apparatus 3, or may be configured as an interface that is integrated with the main body apparatus 3.

Next, operations and the like of the optical scanning observation system 1 having the above described configuration will be described.

First, a specific example of a method for acquiring measured electric current values to be stored in the memory 16 will be described.

For example, when manufacturing the endoscope 2, in a state in which the endoscope 2 is placed under an environment such that the temperature of the actuator portion 15 becomes a predetermined temperature TEM, a factory worker connects the respective parts of the optical scanning observation system 1 and turns on the power supply to the optical scanning observation system 1. Note that the predetermined temperature TEM is a temperature that belongs within a normal temperature range, for example, 25° C.

Thereafter, by, for example, operating a scanning start switch (unshown) of the input apparatus 5, the factory worker issues an instruction to the controller 25 to start scanning by the endoscope 2.

When it is detected that the scanning start switch of the input apparatus 5 was operated and also that measured electric current values that should be read in from the memory 16 do not exist, based on control information that is read in from the memory 24, the scanning control portion 25b controls the driver unit 22 to generate drive signals so that, for example, maximum amplitudes of the signal waveforms shown in FIG. 3 become an amplitude Ha. Note that, for example, the maximum amplitude Ha is set according to the size of an angle of view when the drive signals having the signal waveforms shown in FIG. 3 are supplied to the actuator portion 15 from the driver unit 22 and an object is scanned.

The electric-current measurement portion 22a measures a maximum electric current value I1 of the first drive signal that is supplied from the driver unit 22 to the piezoelectric elements 15a and 15c of the actuator portion 15, and outputs the measured maximum electric current value I1 to the scanning control portion 25b. Further, the electric-current measurement portion 22a measures a maximum electric current value I2 of the second drive signal that is supplied from the driver unit 22 to the piezoelectric elements 15b and 15d of the actuator portion 15, and outputs the measured maximum electric current value I2 to the scanning control portion 25b.

The scanning control portion 25b stores the maximum electric current values I1 and I2 that are outputted from the electric-current measurement portion 22a in the memory 16 as measured electric current values, and thereafter performs control with respect to the image generation portion 25c to display on the display apparatus 4 a character string or the like, for notifying the factory worker to the effect that processing relating to acquisition of the measured electric current values is completed.

That is, according to the above described method, the maximum electric current value I1 which is measured at a time that the first drive signal which is a signal such that the maximum amplitude thereof becomes Ha is supplied to the actuator portion 15 having the predetermined temperature TEM, and the maximum electric current value I2 which is measured at a time that the second drive signal which is a signal such that the maximum amplitude thereof becomes Ha is supplied to the actuator portion 15 having the predetermined temperature TEM are stored in advance in the memory 16 as measured electric current values.

Next, a specific example of processing and the like that is performed when correcting the amplitudes of drive signals supplied from the driver unit 22 to the actuator portion 15 based on the measured electric current values stored in the memory 16 will be described. Note that, hereunder, for simplicity, an example will be described of a case where the maximum electric current values I1 and I2 are stored as the same measured electric current value IM in the memory 16.

Before a user such as a surgeon performs an observation inside a body cavity of a subject, the user connects the respective parts of the optical scanning observation system 1 and turns on the power.

Upon the connector portion 61 of the endoscope 2 and the connector receiving portion 62 of the main body apparatus 3 being connected and the power of the main body apparatus 3 being turned on, the scanning control portion 25b reads in the measured electric current value IM stored in the memory 16. Thereafter, the scanning control portion 25b reads in an amplitude correction parameter that corresponds to the measured electric current value IM read in from the memory 16, from among the respective amplitude correction parameters included in the correction table stored in the memory 24.

Figure 6:
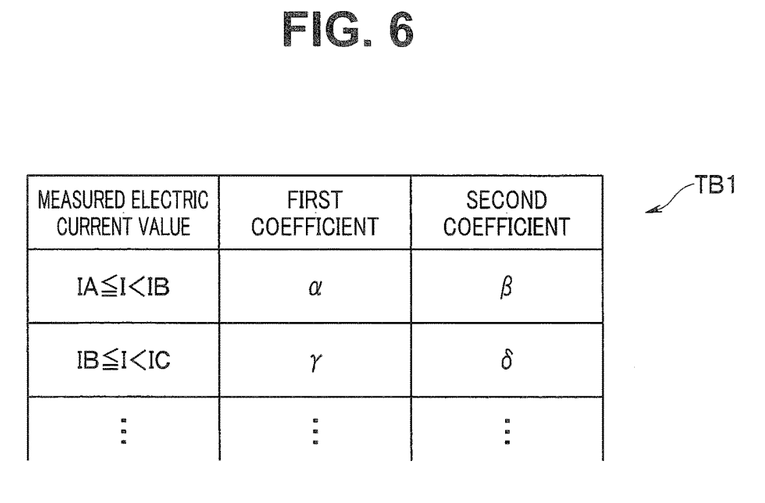
FIG. 6 is a view illustrating an outline of a correction table.

In the present embodiment, for example, a correction table TB1 as shown in FIG. 6 is stored in the memory 24. FIG. 6 is a view illustrating an outline of a correction table that is used for processing of the optical scanning observation system according to the present embodiment.

As illustrated in FIG. 6, the correction table TB1 includes a plurality of amplitude correction parameters that include a combination of a first coefficient and a second coefficient which are set in advance according to the sizes of measured electric current values read in from the memory 16, that is, the sizes of electric current values measured by the electric-current measurement portion 22a when the temperature of the actuator portion 15 is the predetermined temperature TEM.

For example, in a case where the measured electric current value IM read in from the memory 16 is equal to or greater than IA and is less than IB, the scanning control portion 25b reads in a combination of a first coefficient α and a second coefficient β from among the respective amplitude correction parameters included in the correction table TB1 stored in the memory 24. Further, for example, in a case where the measured electric current value IM read in from the memory 16 is equal to or greater than IB and is less than IC, the scanning control portion 25b reads in a combination of a first coefficient γ (where, γ<α) and a second coefficient δ from among the respective amplitude correction parameters included in the correction table TB1 stored in the memory 24.

After connecting the respective parts of the optical scanning observation system 1 and turning on the power, the user issues an instruction for starting scanning by the endoscope 2 to the controller 25 by, for example, operating the scanning start switch of the input apparatus 5.

Upon detecting operation of the scanning start switch, the scanning control portion 25b performs control with respect to the driver unit 22 so as to, for example, generate drive signals having the signal waveforms illustrated in FIG. 3 based on control information read in from the memory 24.

In this case, it is considered that a relation that is expressed as a linear function in the following equation (1) holds between an amplitude H of a drive signal supplied to the actuator portion 15 and an electric current value I measured by the electric-current measurement portion 22a. Note that P and Q in the following equation (1) each represent a constant.

$$H = P \times I + Q \qquad (1)$$

The scanning control portion 25b, for example, monitors a maximum amplitude Hb while calculating the size of the maximum amplitude Hb in accordance with a maximum electric current value Ib outputted from the electric-current measurement portion 22a by using a relational expression obtained by substituting the first coefficient read in from the correction table TB1 for the constant P of the above described equation (1) and substituting the second coefficient read in from the correction table TB1 for the constant Q of the above described equation (1).

Specifically, in a case where, for example, the first coefficient α and the second coefficient β are read in from the correction table TB1, the scanning control portion 25b monitors the maximum amplitude Hb while calculating the maximum amplitude Hb in accordance with the maximum electric current value Ib outputted from the electric-current measurement portion 22a using a relational expression Hb=α×Ib+β.

Further, in a case where the scanning control portion 25b calculated the maximum amplitude Hb using, for example, the relational expression Hb=α×Ib+β, the scanning control portion 25b performs control with respect to the driver unit 22 to generate respective drive signals having corrected amplitudes obtained by correcting the amplitudes (respective amplitudes including the maximum amplitude) of the drive signals supplied from the driver unit 22 to the actuator portion 15 to values obtained by multiplying the respective amplitudes by {Ha/(α×Ib+β)}.

That is, the scanning control portion 25b is equipped with a function as a correction processing portion, and reads in from the correction table TB1 in the memory 24 the first and second coefficients corresponding to the size of the measured electric current value IM read in from the memory 16, and performs correction processing for correcting the scanning range of the endoscope 2 based on the first and second coefficients that are read in. In addition, the scanning control portion 25b uses the first and second coefficients that were read in from the correction table TB1 of the memory 24 to calculate a driving voltage (maximum amplitude Hb) that is in accordance with the electric current value measured by the electric-current measurement portion 22a, and performs correction processing to correct the calculated driving voltage in accordance with a driving voltage (maximum amplitude Ha) when the measured electric current value IM was measured.

In this connection, in a case where the maximum amplitude of a drive signal supplied to the actuator portion 15 is constant, it is considered that the relation between the electric current value of the drive signal supplied to the actuator portion 15 and the temperature of the actuator portion 15 can be expressed with a linear function. Further, a relation expressed as the linear function of the above described equation (1) holds between the amplitude of a drive signal supplied to the actuator portion 15 and an electric current value of the relevant drive signal. Therefore, in order to make the scanning range of the endoscope 2 approximately constant irrespective of changes in the temperature of the actuator portion 15, for example, it is necessary to perform processing which suppresses variations in the maximum amplitude Hb of a drive signal supplied to the actuator portion 15 that has an arbitrary temperature with respect to the maximum amplitude Ha of the drive signal supplied to the actuator portion 15 that has the predetermined temperature TEM.

Further, according to the aforementioned processing using the correction table TB1, based on the above described equation (1) in which the first and second coefficients that are read in from the correction table TB1 are applied as an amplitude correction parameter that corresponds to the size of the measured electric current value IM, and the maximum electric current value Ib that is outputted from the electric-current measurement portion 22a, the maximum amplitude Hb of the drive signal that is supplied from the driver unit 22 to the actuator portion 15 is corrected and caused to match the maximum amplitude Ha. Therefore, according to the aforementioned processing using the correction table TB1, the scanning range of the endoscope 2 can be made approximately constant irrespective of changes in the temperature of the actuator portion 15.

Note that, according to the present embodiment, a configuration may also be adopted so that processing relating to correction of the amplitude of a drive signal supplied from the driver unit 22 to the actuator portion 15 is performed at a predetermined timing such as a timing at which an operation of a predetermined switch of the input apparatus 5 is detected by the scanning control portion 25b.

Figure 7:
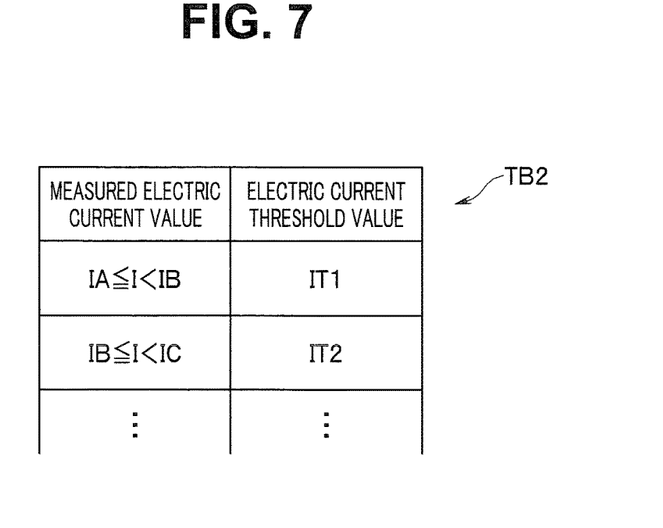
FIG. 7 is a view illustrating an outline of a threshold value table that is used in processing of the optical scanning observation system according to the embodiment.

Further, according to the present embodiment, in addition to the correction table TB1 shown in FIG. 6, for example, a threshold value table TB2 as shown in FIG. 7 may also be stored in the memory 24. A specific example of processing and the like performed in this case is described hereunder. FIG. 7 is a view illustrating an outline of a threshold value table that is used for processing of the optical scanning observation system according to the present embodiment. Note that, hereunder, for simplicity, a specific description relating to sections at which processing and the like described previously can be applied is omitted as appropriate.

As illustrated in FIG. 7, a threshold value table TB2 includes a plurality of electric current threshold values which are set in advance in accordance with the sizes of measured electric current values which are read in from the memory 16.

Specifically, for example, in a case where the measured electric current value IM that is read in from the memory 16 is equal to or greater than IA and is less than IB, the scanning control portion 25b reads in an electric current threshold value IT1 from among respective electric current threshold values included in the threshold value table TB2 stored in the memory 24. Further, in a case where, for example, the measured electric current value IM that is read in from the memory 16 is equal to or greater than IB and is less than IC, the scanning control portion 25b reads in an electric current threshold value IT2 (where, IT2>IT1) from among the respective electric current threshold values included in the threshold value table TB2 stored in the memory 24.

Thereafter, the scanning control portion 25b, for example, uses a relational expression obtained by substituting the first coefficient read in from the correction table TB1 for the constant P of the above described equation (1) and substituting the second coefficient read in from the correction table TB1 for the constant Q of the above described equation (1) to calculate the size of the maximum amplitude Hb in accordance with the maximum electric current value Ib of a drive signal that is currently being supplied from the driver unit 22 to the actuator portion 15.

Specifically, in a case where, for example, the first coefficient $\alpha$ and the second coefficient $\beta$ are read in from the correction table TB1, the scanning control portion 25b uses the relational expression Hb=$\alpha \times$Ib+$\beta$ to calculate the size of the maximum amplitude Hb in accordance with the maximum electric current value Ib of a drive signal that is currently being supplied from the driver unit 22 to the actuator portion 15.

Further, in a case where the scanning control portion 25b calculated the maximum amplitude Hb using, for example, the relational expression Hb=$\alpha \times$Ib+$\beta$, and reads in the electric current threshold value IT1 from the threshold value table TB2, at a timing at which it is detected that the maximum electric current value Ib exceeds the electric current threshold value IT1, the scanning control portion 25b performs control with respect to the driver unit 22 to generate respective drive signals having corrected amplitudes obtained by correcting the amplitudes (respective amplitudes including the maximum amplitude) of the drive signals supplied from the driver unit 22 to the actuator portion 15 to values obtained by multiplying the respective amplitudes by {Ha/($\alpha \times$Ib+$\beta$)}.

That is, the scanning control portion 25b reads in from the correction table TB1 in the memory 24 the first and second coefficients corresponding to the size of the measured electric current value IM that is read in from the memory 16 and reads in from the threshold value table TB2 in the memory 24 an electric current threshold value corresponding to the size of the measured electric current value IM, and when an electric current value (maximum electric current value Ib) exceeding the electric current threshold value that was read in is measured by the electric-current measurement portion 22a, also performs correction processing for correcting the scanning range of the endoscope 2 based on the first and second coefficients that were read in.

According to the aforementioned processing using the correction table TB1 and the threshold value table TB2, the maximum amplitude Hb of the drive signal that is supplied from the driver unit 22 to the actuator portion 15 is corrected and caused to match the maximum amplitude Ha based on the above described equation (1) in which the first and second coefficients that are read in from the correction table TB1 are applied as an amplitude correction parameter corresponding to the size of the measured electric current value IM, an electric current threshold value that is read in from the threshold value table TB2 in accordance with the size of the measured electric current value IM, and the maximum electric current value Ib outputted from the electric-current measurement portion 22a. Therefore, according to the aforementioned processing using the correction table TB1 and the threshold value table TB2, the scanning range of the endoscope 2 can be made approximately constant irrespective of changes in the temperature of the actuator portion 15.

As described above, according to the present embodiment, for example, prior to the use of the endoscope 2 by a user, by performing the simple work of measuring the measured electric current values IM (maximum electric current values I1 and I2) supplied to the actuator portion 15 having the predetermined temperature TEM and storing the measured values in the memory 16 in advance, when the endoscope 2 is used by a user, the maximum amplitude Hb of a drive signal supplied from the driver unit 22 to the actuator portion 15 can be corrected so as to match the maximum amplitude Ha at the time that the measured electric current values IM (maximum electric current values I1 and I2) were measured. Thus, according to the present embodiment, work for acquiring information to be used for correction of the temperature dependence of a scanning range of a scanning endoscope can be simplified.

It should be understood that the present invention is not limited to the respective embodiments described above, and naturally various modifications and applications are possible without departing from the spirit of the invention.

What is claimed is:

1. An optical scanning observation system, comprising:
   an endoscope including an optical scanner that scans an object with an illuminating light that is emitted from a light source;
   a drive signal generator configured to generate a drive signal, an amplitude of the drive signal being in accordance with a driving voltage applied to the optical scanner;
   an electric-current meter configured to measure an electric current value of the drive signal that is supplied from the drive signal generator to the optical scanner;
   one or more storage devices configured to store the electric current value measured by the electric-current meter when a temperature of the optical scanner is a predetermined temperature; and store a plurality of correction parameters that are set in advance according to a size of the measured electric current value; and
   a processor comprising hardware, the processor being configured to:
     read the size of the measured electric current value from the one or more storage devices; select one or more correction parameters from the plurality of correction parameters stored in the one or more storage devices based on the read size of the measured electric current value; and
     perform correction processing for correcting the amplitude of the drive signal based on the selected one or more correction parameters.

2. The optical scanning observation system according to claim 1, wherein to perform the correction processing, the processor is further configured to:
 calculate the driving voltage in accordance with the electric current value measured by the electric-current meter using the selected one or more correction parameters; and
 correct the calculated driving voltage to match a driving voltage at a time that the measured electric current value is measured.

3. The optical scanning observation system according to claim 1, wherein:
 the one or more storage devices are further configured to: store a plurality of threshold values that are previously set according to the size of the measured electric current value; and
 the processor is further configured to:
  select a threshold value from the plurality of threshold values stored in the one or more storage devices based on the read size of the measured electric current value; and
  perform the correction processing when the electric current value measured by the electric-current meter exceeds the selected threshold value.

4. The optical scanning observation system according to claim 1, wherein when the size of the measured electric current value is smaller than a predetermined value, the processor is further configured to: select a first group of correction parameters from the plurality of correction parameters; and perform the correction processing for correcting the amplitude of the drive signal based on the selected first group of correction parameters, and
 wherein when the size of the measured electric current value is equal to or greater than the predetermined value, the processor is further configured to: select a second group of correction parameters from the plurality of correction parameters; and perform the correction processing for correcting the amplitude of the drive signal based on the selected second group of correction parameters.

* * * * *